US012661024B2

(12) United States Patent
Imtiaz et al.

(10) Patent No.: US 12,661,024 B2
(45) Date of Patent: Jun. 23, 2026

(54) METHODS OF AND APPARATUS FOR MEASURING PHYSIOLOGICAL PARAMETERS

(71) Applicant: Acurable Limited, London (GB)

(72) Inventors: Syed Anas Imtiaz, London (GB); Esther Rodriguez-Villegas, London (GB); Piyush Sharma, London (GB)

(73) Assignee: Acurable Limited, London (GB)

( * ) Notice: Subject to any disclaimer, the term of this patent is extended or adjusted under 35 U.S.C. 154(b) by 1202 days.

(21) Appl. No.: 17/343,663

(22) Filed: Jun. 9, 2021

(65) Prior Publication Data

US 2021/0298623 A1 Sep. 30, 2021

Related U.S. Application Data

(63) Continuation of application No. PCT/GB2019/053544, filed on Dec. 13, 2019.

(30) Foreign Application Priority Data

Dec. 14, 2018 (GB) ...................................... 1820433

(51) Int. Cl.
A61B 5/024 (2006.01)
A61B 5/00 (2006.01)
(Continued)

(52) U.S. Cl.
CPC ...... *A61B 5/02438* (2013.01); *A61B 5/02141* (2013.01); *A61B 5/0235* (2013.01);
(Continued)

(58) Field of Classification Search
CPC .... A61B 2560/0209; A61B 2560/0242; A61B 2560/029; A61B 2562/0204; A61B 5/02116; A61B 5/02141; A61B 5/0235; A61B 5/02438; A61B 5/02444; A61B 5/489; A61B 5/6824; A61B 5/6831;
(Continued)

(56) References Cited

U.S. PATENT DOCUMENTS 4,549,550 A 10/1985 Kami
5,191,889 A 3/1993 Mornhinweg et al.
(Continued)

FOREIGN PATENT DOCUMENTS

CN 104053401 A 9/2014
CN 107595245 A 1/2018
(Continued)

OTHER PUBLICATIONS

Search Report dated May 31, 2019, for United Kingdom Patent Application No. GB1820433.9.
(Continued)

*Primary Examiner* — Eric J Messersmith
(74) *Attorney, Agent, or Firm* — Withrow + Terranova, PLLC; Vincent K. Gustafson

(57) ABSTRACT

The present invention relates to apparatus for measuring physiological parameters in a blood vessel. The apparatus comprises at least one acoustic sensor positionable on a part of a subject's body which is configured to receive an acoustic signal from a target blood vessel. The acoustic sensor is attached to the part of the subject's body by an attachment means.

13 Claims, 25 Drawing Sheets

(51) Int. Cl.
   *A61B 5/021* (2006.01)
   *A61B 5/0235* (2006.01)
(52) U.S. Cl.
   CPC .......... *A61B 5/6824* (2013.01); *A61B 5/7203* (2013.01); *A61B 2562/0204* (2013.01)
(58) Field of Classification Search
   CPC ... A61B 5/6844; A61B 5/7203; A61B 5/7214; A61B 7/04; A61B 7/045
   See application file for complete search history.

(56) References Cited

U.S. PATENT DOCUMENTS

| | | | |
|---|---|---|---|
| 5,406,953 A | | 4/1995 | Bui |
| 10,842,968 B1 * | | 11/2020 | Kahn ................. G06F 16/9537 |
| 2005/0010119 A1 | | 1/2005 | Palti et al. |
| 2007/0113654 A1 | | 5/2007 | Carim et al. |
| 2010/0217345 A1 | | 8/2010 | Wolfe et al. |
| 2014/0128753 A1 | | 5/2014 | Luna et al. |
| 2015/0094551 A1 | | 4/2015 | Frix et al. |
| 2015/0099998 A1 | | 4/2015 | Christensen et al. |
| 2016/0026212 A1 * | | 1/2016 | Lee ....................... G06F 1/3231 |
| | | | 361/679.03 |
| 2016/0206277 A1 * | | 7/2016 | Bidichandani ......... A61B 7/026 |
| 2016/0287103 A1 | | 10/2016 | Saponas et al. |
| 2016/0374608 A1 | | 12/2016 | Dugan |
| 2018/0070841 A1 * | | 3/2018 | Honore .............. A61B 5/02007 |
| 2018/0317789 A1 | | 11/2018 | Ransbury et al. |
| 2019/0076084 A1 | | 3/2019 | Kanegae et al. |

FOREIGN PATENT DOCUMENTS

| | | | |
|---|---|---|---|
| IN | 201611026380 | A | 7/2017 |
| JP | 2009011555 | A | 1/2009 |
| WO | 2013184315 | A1 | 12/2013 |
| WO | 2014149954 | A1 | 9/2014 |
| WO | 2018013656 | A1 | 1/2018 |
| WO | 2018/183558 | A1 | 10/2018 |

OTHER PUBLICATIONS

International Search Report, International Application No. PCT/GB2019/053544, dated Jun. 25, 2020.
Written Opinion of the International Search Authority, International Application No. PCT/GB2019/053544, dated Jun. 25, 2020.
Second Examination Report dated Oct. 5, 2022, for United Kingdom Patent Application No. GB1820433.9.
Office Action for Canadian Patent Application No. 3,122,667 mailed Mar. 6, 2024, 4 pages.
Search Report for Chinese Patent Application No. 2019800818571 mailed Feb. 22, 2024, 3 pages.
First Office Action for Chinese Patent Application No. 2019800818571 mailed Feb. 23, 2024, 11 pages.
Notice of Acceptance for Australian Patent Application No. 2019398725, mailed Nov. 15, 2023, 4 pages.
Examination Report for European Patent Application No. 19823958.4, mailed Jul. 13, 2023, 5 pages.
Office Action for Canadian Patent Application No. 3,122,667 mailed Apr. 8, 2026, 4 pages.

* cited by examiner 117    119    108    106    120

118

105

506

507

508

601                                                          603

602

701	705	703

702

801

802

804

803

1201

1202

1203                                              1204

1301

1302

1303

1304

1405

1401

1402

1403

1404

METHODS OF AND APPARATUS FOR MEASURING PHYSIOLOGICAL PARAMETERS

CROSS REFERENCE TO RELATED APPLICATIONS

Continuation of International Application No. PCT/GB2019/053544 filed on Dec. 13, 2019. Priority is claimed from British Application No. 1820433.9 filed on Dec. 14, 2018. Both the foregoing applications are incorporated herein by reference in their entirety.

STATEMENT REGARDING FEDERALLY SPONSORED RESEARCH OR DEVELOPMENT

Not Applicable

NAMES OF THE PARTIES TO A JOINT RESEARCH AGREEMENT

Not Applicable.

BACKGROUND

Field

The present invention relates to a device for non-invasive measurement of physiological parameters through determining acoustic properties of target blood vessels in a subject's body. The present invention further includes methods of non-invasive measurement of physiological parameters through determining acoustic properties of target blood vessels in a subject's body and computer applications and/or software for evaluation of the same.

Background

Continuous monitoring of certain physiological parameters, i.e. pulse, heart rate variability, and blood pressure, is desirable in many different circumstances. For example, elderly or disabled persons, or those suffering from one of many medical conditions where an increase in pulse or blood pressure could be dangerous, would benefit from monitoring to notify the person or somebody else in the event an event occurs resulting in an abnormal change in measurement of certain physiological parameters.

There are many examples of devices that can continuously monitor pulse and other heart related parameters. Chest straps incorporating a set of electrode leads have been in existence for years. Modern chest straps incorporate a transmitter which sends a simple radio pulse or coded signal from the chest strap to a receiver (typically a wrist mounted device, cycle computer or mobile phone). The receiver identifies and receives the signal from the chest strap and displays data representative of a measured physiological parameter.

More recently, some smart watches and other wrist mounted devices incorporate an optical sensor that is capable of measuring variation in blood flow by shining a light from an LED through the skin and measuring how the light is absorbed, refracted or reflected by target blood vessels. Such optical sensors can often determine other physiological parameters such as, but not limited to, blood oxygen saturation.

Each of the above devices has shortcomings in connection with certain intended uses. Chest straps can typically only measure heart rate. While this is ideal for athletic activities such as running and cycling, the derivable data is of limited use when monitoring persons for changes in medical condition. Optical sensors have greater applicability but accuracy is compromised when the optical sensor is not firmly placed against the person's skin. This requires the watch, or other wrist mounted device, to be strapped tightly to the person's wrist which is uncomfortable. Further, during vigorous exercise and where the watch is not strapped tightly to the person's wrist, the watch tends to move in two dimensions of freedom thus compromising the sensor's ability to measure refraction of the light from the LED off the person's blood vessels. Optical sensors used to continuously monitor physiological parameters also tend to drain device batteries quickly.

The present invention seeks to provide improved devices for and methods of measurement of physiological parameters and signals.

SUMMARY

For the purposes of the claimed inventions, reference to acoustic sensors shall be interpreted as including, but not being limited to, microphones, piezoelectric sensors and other pressure sensors. It will be appreciated by the skilled person that the presently disclosed method and device may have applications for animal, particularly veterinary, use.

An aspect of the invention provides apparatus for measuring physiological parameters in a target blood vessel comprising at least one acoustic sensor positionable on a part of the subject's body and a means for attachment of the acoustic sensor to said part of the subject's body, wherein the at least one acoustic sensor is configured to receive an acoustic signal from a target blood vessel.

Global fatalities from conditions such as heart disease show a year on year increasing trend largely because of longer lifespans in many developed nations and obesity related health conditions. Heart related health conditions often go undetected until such conditions cause the exhibiting of significant effects on a subject's health. Even once heart conditions have been diagnosed, monitoring is generally periodic at regular check-ups and a change in condition may not be immediately apparent to a subject or their health professional. The present invention seeks to provide a wearable device that can be worn on a subject's limb for the purpose of continually monitoring certain physiological signals such as heart rate, S1-S4 heart sounds, heart rate variability, respiratory rate blood pressure and apnoea events, for example. Such monitoring is provided by measuring acoustic signals from target blood vessels, preferably blood vessels located in the subject's forearm. The applicant has found that acoustic signals from a targeted blood vessels can provide an output representative of S1-S4 heart sounds, heart rate, heart rate variability, diastolic and systolic pressure, or respiratory rate, for example, that is comparable with traditional periodic monitoring such as by way of electrocardiogram.

In one embodiment, the acoustic sensor comprises a first microphone, a second microphone and a processor for receiving signals from the first microphone and second microphone, wherein the first microphone is configured to measure an acoustic signal from target blood vessel and the second microphone is configured to determine background noise and the processor is configured to remove the background noise determined by the second microphone from the acoustic signal measured by the first microphone.

In practice, measuring acoustic signals of a target blood vessel from outside of the subject's body involves listening for sound waves at a frequency as low as 10 Hz. Any background noise is likely to have a higher frequency than 10 Hz and thus is likely to mask acoustic signals from target blood vessel. To counter this, embodiments of the present invention use a first microphone to measure acoustic signals from a target blood vessel and a second microphone to monitor environmental noise. The processor removes environmental noise from the measured acoustic signal to produce a derived output.

In another embodiment, the apparatus further comprises an optical sensor including a light source and a photosensor, wherein the photosensor is configured to measure one or more properties of the light source through absorption, refraction or reflection of the light source from a target blood vessel.

To ensure an accurate reading from an acoustic sensor, it is important for the acoustic sensor to be located in close proximity with a target blood vessel. Visual positioning on a subject's limb, i.e. forearm, is very much trial and error and it is quite likely that the acoustic sensor will not be positioned correctly. To reduce the risk of incorrect positioning, an optical sensor may be provided that includes a light source, i.e. a LED, fibre optic or laser, for example, and a photosensor. In use, the light source shines a light on the subject's skin and is absorbed, refracted or reflected in a different way depending on whether the light source is directly above a target blood vessel or not. The photosensor measures the absorption, refraction or reflection of the light source to determine one or more properties of the light source. This measurement can be used to determine whether the acoustic sensor is positioned correctly or not.

In another embodiment, the apparatus further comprises a temperature sensor, wherein the temperature sensor measures the temperature of a surface to which it is attached and the processor determines whether the measured temperature is indicative of the apparatus being in contact with a subject's skin or not.

As above, it is important for the acoustic sensor to be located in close proximity with a target blood vessel. For general positioning and to determine whether the apparatus is being worn or not, the temperature sensor advantageously provides a measure of local temperature which is used by the processor to determine whether the temperature is within the range that would typically represent the surface temperature of a subject's skin. This determination can be used by the processor to determine whether to provide power to other electronic components of the apparatus in conjunction with measurements obtained by other sensors.

In another embodiment, the means for attachment of the acoustic sensor on the limb comprise a sensor housing and an attachment interface having a first attachment configuration and a second attachment configuration such that when the attachment interface is in the first attachment configuration, the sensor housing can be moved in three degrees of freedom relative to the attachment interface and when the attachment interface is in the second attachment configuration, the sensor housing is positionally fixed relative to the attachment interface.

As described above, the position of the acoustic sensor is important to ensure that accurate measurements are obtained. To protect the acoustic sensor it is enclosed within a sensor housing. The sensor housing is attachable to a subject's limb by way of an attachment interface, i.e. a strap. Due to the potential difficulty in correctly locating the sensor housing at the first attempt the attachment interface of the present invention advantageously enables the sensor housing to be loosely positioned relative to the attachment interface so as to hold the sensor housing in place. Application of a reasonable force would still be required to move the sensor housing relative to the attachment interface but a subject would be able to apply sufficient force to move the sensor housing translationally in the x and y dimensions as well as rotationally around the y axis. Once the sensor housing is determined to be in the correct position the attachment interface is moved from the first configuration where the sensor housing is moveable relative to the attachment interface to the second configuration where the sensor housing is positionally fixed relative to the attachment interface. Such a configuration advantageously enables small amounts of adjustment of the sensor housing to ensure positioning is correct. In other embodiments, the apparatus may be fixed in position by a strong adhesive.

In another embodiment the apparatus further comprises a transmitter for sending acoustic signals measured by the acoustic sensor to an external electronic device.

The present invention enables certain physiological parameters to be continually monitored by the acoustic sensor. The transmitter enables the values of such parameters to be transmitted to an external device, i.e. a cell phone, computer or the cloud via a router. Use of suitable software on the external device enables monitoring of selected parameters either by the subject wearing the apparatus, a family member or healthcare professional.

In another embodiment, the apparatus further comprises a motion sensor for determining whether the apparatus is being worn by a subject, wherein the apparatus is configured to only activate the acoustic sensor and/or photosensor when the motion sensor determines motion representative of the apparatus being worn by a subject.

Battery life is a significant issue that needs to be considered during design of wearable electronic devices. The more sensors that are active at any one time, the greater the battery drain. Accordingly, it is desirable to only activate sensors such that they are able to draw battery power when an electronic device is being worn. This desire needs to be balanced with ease of use for a user of the device. Consequently, it is not always desirable for the user to have to manually turn sensors on and off. To achieve this balance, the present invention uses a motion sensor to determine whether the apparatus is being worn. This determination is made by the motion sensor, i.e. an accelerometer, measuring changes in motion, i.e. acceleration, over a period of time. If the type and frequency of motion is determined to be representative of the apparatus being worn by a user, one or more sensors and surrounding electronics are automatically activated without user intervention.

Conversely, if the type and frequency of motion is determined not to be representative of the apparatus being worn by a user, no sensors and surrounding electronics are activated and if any sensors are already activated they are automatically deactivated without user intervention. The temperature sensor (as described above) may be activated only when the motion sensor detects motion of the apparatus. The optical sensor (also as described above) may be activated only once the temperature sensor measures a temperature indicative of the apparatus being worn. It will be appreciated that the order of activation can be varied depending on application.

In another embodiment the apparatus configured to activate the first and second microphones when the photosensor determines light absorption, refraction or reflection representative of the apparatus being located in close proximity to target blood vessel.

To further optimise battery drain, the first and second microphones are only activated when the photosensor of the optical sensor provides an absorption, refraction or reflection measurement corresponding to an expected measurement if the sensor housing is located in close proximity with a target blood vessel. Other electronic components may also only be powered when the sensor is determined to be in close proximity with a target blood vessel. This in conjunction with the optical sensor only being activated when the apparatus is determined to be worn by a subject reduces battery drain when the apparatus is either not in use or when it is incorrectly fitted.

Another aspect of the invention provides a system for measuring physiological parameters from a target blood vessel and an electronic device configured to receive signals from a sensor and display one or more data fields representative of physiological parameters measured by the sensor.

Another aspect of the invention provides a method of fitting an acoustic sensor in proximity to target a target blood vessel, the method comprising: i) using an optical sensor to determine that a device including a sensor for measurement of physiological parameters is located within a predetermined threshold distance of a target blood vessel; ii) sending a signal to an external device to indicate that the device is not located in close proximity to the target blood vessel if the location of the optical sensor is above the predetermined threshold distance; and iii) sending a signal to an external device to indicate that the device is located in close proximity to the target blood vessel if the location of the optical sensor is not above the predetermined threshold distance.

Another aspect of the invention provides a method of determining whether an acoustic sensor is being worn by a subject, the method comprising: i) using a sensor to measure a parameter of a device and determine whether such parameter is representative of the device being worn by a subject; ii) activating an acoustic and/or optical sensor if the sensor measures a parameter that is representative of the device being worn by a subject; and iii) deactivating the acoustic and/or optical sensor if the sensor does not measure a parameter that is representative of the device being worn by a subject after lapse of a time period above a predetermined threshold.

The parameter may be motion or temperature, for example.

Another aspect of the invention provides a method of measuring physiological parameters in a blood vessel, the method comprising: i) using the motion sensor of the apparatus of present disclosure to measure the position and/or motion of a part of the subject's body, and ii) measuring a physiological parameter in the blood vessel only when the part of the subject's body is determined to be in the desired position or performing the desired motion.

Another aspect of the invention provides a method of measuring physiological parameters in a blood vessel, the method comprising: i) using the motion sensor of the apparatus of present disclosure to measure the position and/or motion of a part of the subject's body, ii) indicating a desired position and/or motion of the part of the subject's body, and iii) measuring a physiological parameter in the blood vessel only when the part of the subject's body is determined to be in the desired position or performing the desired motion.

Another aspect of the invention provides a method of measuring physiological parameters in a blood vessel, the method comprising: i) using the motion sensor of the apparatus of present disclosure to measure the position and/or motion of a part of the subject's body, ii) indicating a desired position and/or motion of the part of the subject's body, iii) providing feedback to the user to indicate whether the part of the subject's body is in the desired position or performing the desired motion, or not, and iii) measuring a physiological parameter in the blood vessel only when the part of the subject's body is determined to be in the desired position or performing the desired motion.

Another aspect of the invention provides a method of measuring physiological parameters in a blood vessel, the method comprising: i) using the motion sensor of the apparatus of present disclosure to measure the position and/or motion of a part of the subject's body, ii) using the level of movement to mark the measured physiological signal as artefact corrupted.

Another aspect of the invention provides a method of measuring physiological parameters in a blood vessel, the method comprising: i) using the motion sensor of the apparatus of present disclosure to measure the position and/or motion of a part of the subject's body; ii) determining correlations between the measured levels of movement and cardiac parameters obtained from the measured physiological signal.

Another aspect of the invention provides apparatus for measuring blood pressure comprising an inflatable rubber bladder configured for attachment around a subject's limb, means for inflating the inflatable rubber bladder around the subject's limb, a valve for releasing pressure from the inflatable bladder and apparatus for identifying acoustic signals, wherein the apparatus records systolic blood pressure at the point certain feature values of acoustic signals are detected following inflation of the inflatable rubber bladder and subsequent partial release of pressure from the inflatable rubber bladder and further records diastolic pressure at the point other features values of the acoustic signals (such as reduction of power) are detected following further release of pressure from the inflatable rubber bladder. In both cases the features might be related to the Korotkoff sounds.

Another aspect of the invention provides a method of determining blood pressure, the method comprising: i) measuring a cardiac parameter at a first location of a subject's or animal body; ii) measuring a cardiac parameter at a second location of a subject's or animal body; iii) determining a pulse transient time from the first location to the second location; and iv) extrapolating blood pressure from the pulse transient time.

Another aspect of the invention provides a method of monitoring sleep phases, the method comprising: i) using apparatus according to the present disclosure to monitor any of movement, cardiac parameters and respiratory rate during a predetermined time period, and ii) extrapolating such movement, cardiac parameters and respiratory rate to assign sleep phases to identified segments of the pre-determined time period.

Another aspect of the invention provides a method of identifying cardiac or respiratory related events, the method comprising: i) using the apparatus of the present disclosure to measure one or more physiological parameters, ii) determining whether any of the one or more measured physiological parameters falls above or below a predetermined threshold range, and iii) transmitting an alarm signal if any of the one or more measured physiological parameters falls above or below the predetermined threshold range.

BRIEF DESCRIPTION OF THE DRAWINGS

Embodiments of the present invention will now be described by way of reference to the following figures.

DETAILED DESCRIPTION

Figure 1:
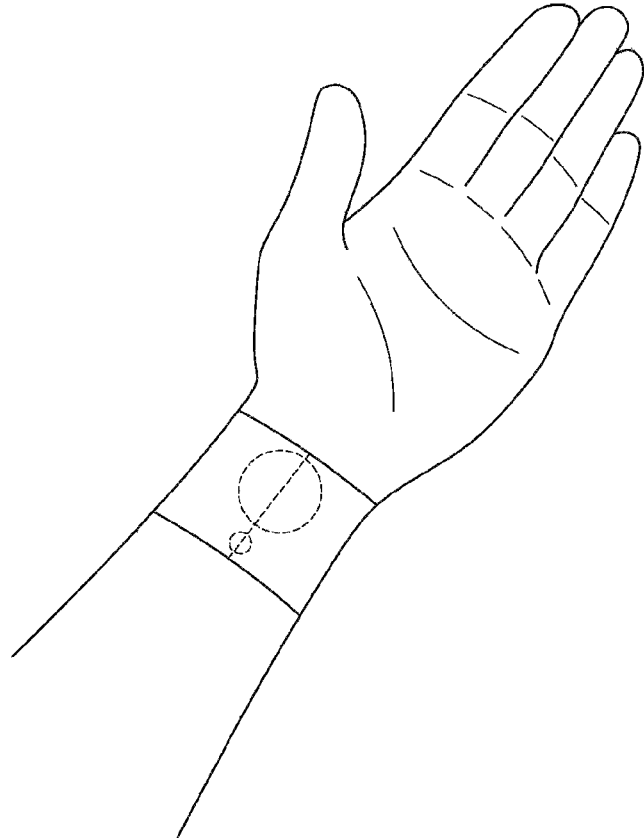
FIG. 1 illustrates apparatus according to certain embodiments of the invention as worn on a subject's forearm.
Figure 2:
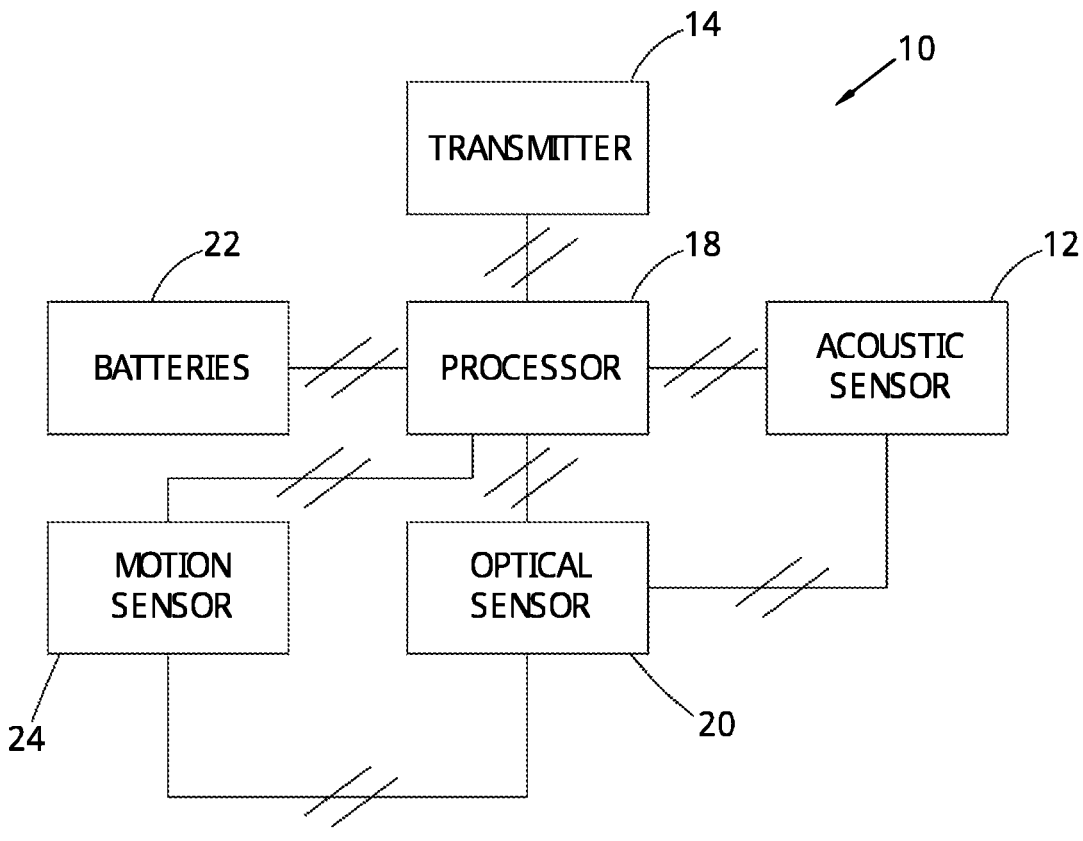
FIG. 2 illustrates features of apparatus of the invention.

In accordance with the figures, the present invention relates to apparatus (10) for measuring physiological parameters in a blood vessel, for example in the forearm or neck. The invention will be described by way of reference to measuring physiological parameters of blood vessels of a person but it will be appreciated that embodiments of the invention are equally applicable to measuring physiological parameters of blood vessels of certain other mammals.

The apparatus (10) in its simplest form comprises an acoustic sensor (12) for receiving acoustic signals and a transmitter (14) for transmitting the received acoustic signal to a receiver (16), i.e. a mobile phone or other computer device. The acoustic signal can be transmitted by the transmitter (14) to the receiver (16) by customized or established communication protocols including but not limited to: Bluetooth®, ANT+, WIFI® and radio signals.

The signal can be transmitted as raw data or it can be converted to subject's readable data within the apparatus before being transmitted. Some embodiments of the invention may include a display screen configured to display subject's readable data representative of the parameter being measured by the apparatus, i.e., heart rate or blood pressure, for example. The raw data and/or subject's readable data can be stored within the apparatus (10) on non-volatile memory. The data may be compressed prior to transmission to reduce packet size and may be encrypted to prevent personal or sensitive data being intercepted.

The acoustic sensor (12) is likely one, or more, microphone(s). In one embodiment the acoustic sensor (12) comprises at least two microphones (12a, 12b). A first microphone (12a) is positioned in close proximity, in use, to a target blood vessel and is configured to measure acoustic signals from the subject's arteries. The frequency of acoustic signal measured by the first microphone may be as low as 10-30 Hz and as high as 10 KHz. A second microphone (12b) is positioned away from the subject's arteries and is configured to measure background noise. The second microphone (12b) may measure acoustic frequencies of between 10 Hz to 10 KHz. A processor (18) is provided for receiving acoustic signals from the first and second microphones (12a, 12b). The processor eliminates noise received by the second microphone (12b) from acoustic signals from the subject's arteries received by the first microphone (12a). The processed signal is then sent by the transmitter (14) to the receiver (16). Data representative of the processed signal is displayed on the receiver (16).

To facilitate accurate positioning of the apparatus in close proximity of the subject's arteries, in particular on the forearm, an optical sensor (20) may be provided. The optical sensor (20) is configured to shine a LED onto the arteries. Refraction and/or absorption of the light emitted by the LED is measured to determine whether the LED is shone on the arteries. The LED can be a single LED or several LEDs, i.e. three LEDs spaced equidistant from a centre point. Reference to LED in the remainder of this document refers to LED singularly or plural LEDs.

If the LED is determined to be shone on the arteries, the first and/or second microphone(s), and other electronic components, are activated and a signal is sent by the transmitter (14) to the receiver (16) to indicate that the apparatus is correctly located. If the LED is determined not to be shone on the arteries, the first and second microphones, and other electronic components, are not activated and a signal is sent by the transmitter (14) to the receiver (16) to indicate that the apparatus (10) is not correctly located. The receiver (16) then displays a visual representation indicating whether the apparatus (10) is located correctly or not.

To further aid the subject in locating the apparatus (10), the optical sensor (20) may map the absorption, refraction or reflection of light from the LED when it is shone on the subject. The mapped light absorption, refraction or reflection is used by the processor (18) to determine the position of the apparatus (10) relative to the subject's arteries. This information is sent by the transmitter (14) to the receiver (16) and the receiver (16) displays a visual representation indicating which direction the apparatus (10) should be moved or rotated for optimal positioning. As the apparatus (10) is moved, the receiver (16) shows the apparatus (10) moving in relation to the determined position of the subject's arteries.

Once the apparatus (10) is in an optimal position relative to the subject's arteries, the position of the apparatus (10) is fixed to prevent further movement. This will be described further below.

To ensure that the acoustic signal received by the first microphone (12a) is strong and not compromised by excessive background noise, the apparatus is provided with a seal (22) between the apparatus (10) and the subject's skin. The first microphone (12a) is acoustically connected to the subject's skin by way of a port within the region of the apparatus bounded by the seal (22). The apparatus (10) may be affixed to a user's skin by way of adhesive to prevent movement of the acoustic sensor(s) (12).

Battery drain is a problem for all wearable devices that are required to be small enough to be practical and comfortable to use yet large enough to contain a plurality of sensors and a large enough battery to power said sensors. Apparatus (10) according to embodiments of the invention therefore incorporates motion sensors (24) such as accelerometers to determine when the apparatus is being worn by a subject. If the motion sensor (24) determines that the apparatus is being moved in a manner consistent with being worn by a subject, the optical sensor (20) is activated to enable the apparatus (10) to be located on the subject's body. Once the apparatus (10) is determined to be properly located, the first and second microphones (12a, 12b), and other electronic components, are activated. In embodiments with no optical sensor, the first and second microphones (12a, 12b), and other electronic components, are activated when it is determined that the apparatus (10) is being worn by a subject. When is it is determined that the apparatus (10) is no longer being worn, the optical sensor (20) and/or first and second microphones (12a, 12b), and other electronic components, are deactivated to conserve battery. Motion sensors incorporated within embodiments of the invention can also be used to identify whether a subject is performing a certain movement under measurement conditions that need to be controlled and if so to give automatic feedback. In one example, the apparatus might be used to take readings at specific times, and at those times the motion sensor(s) can be used to determine whether the subject has got the limb as it needs to be to increase the accuracy of the reading. This might include being at a certain height, angle and static. The motion sensor would detect whether something is not correct and could give feedback to the user to correct this. The feedback can, for example, be given through a display or acoustically. In another example, the motion sensors might be used to correlate physiological outputs to users' levels of activity (for example cardiac patterns, at times with position or movement, or combining both to determine phases of sleep). In another example, these sensors could be used to assist with signal artefacts reduction to assist with the interpretation of the physiological signals of interest, or to eliminate signals when those are considered to be highly corrupted.

The motion sensor can also be configured, in conjunction with the optical sensor and acoustic sensor, to identify and monitor sleep phases and sleep related health conditions such as apnoea.

Figure 3:
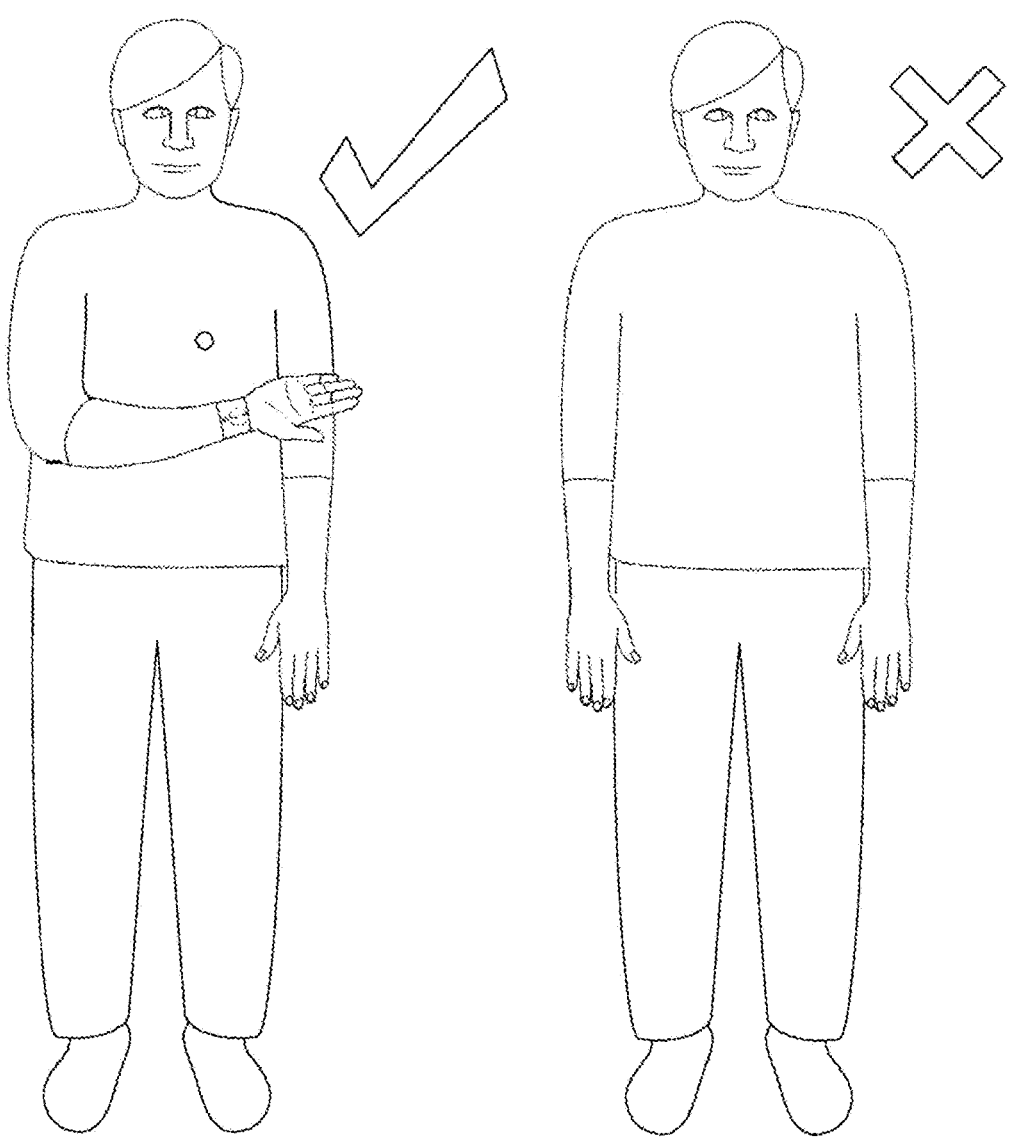
FIG. 3 illustrates an example usage of embodiments of the invention.

Other uses of motion sensors (24) in conjunction with the apparatus (10) include measuring body position and/or motion compared to a reference standard and only taking a measurement of a parameter when the body position and/or motion is within a pre-defined range of the reference standard. In some embodiments a user will be provided with feedback if there is a deviation from the body position and/or motion. The feedback would guide the user to find the correct body position and/or motion. The feedback may be tactile through haptic, visual or acoustic feedback embedded within the apparatus (10) or visual or acoustic through a partner app operable on a smart phone, tablet or other computing device. Furthermore, the motion sensors (24) may allow the processor (18) to correlate a certain body position and/or motion with a cardiac parameter. For example, FIG. 3 illustrates two different positions of a subject's arm. When the arm is elevated towards the subject's heart, the apparatus (10) will measure a predetermined parameter, such as blood pressure. When the subject's arm is by their side, the apparatus (10) will not measure the predetermined parameter. The position and/or motion of a body part can vary depending on application and the parameter to be measured and is not intended to be limited Examples of motion sensors that can be used with embodiments of the invention include, but are not limited to, accelerometers and gyroscopes.

The apparatus (10) is powered by batteries. Some embodiments may provide for batteries to be replaced when depleted. Other embodiments may provide a wired charging port for connection of the apparatus (10) to the mains or portable power source or wireless charging. A battery indicator is provided and indicated the approximate level of charge of the batteries.

FIGS. 4 to 25 illustrate example enclosures for sensors suitable for use with apparatus according to aspects and embodiments of the invention.

Figure 4:
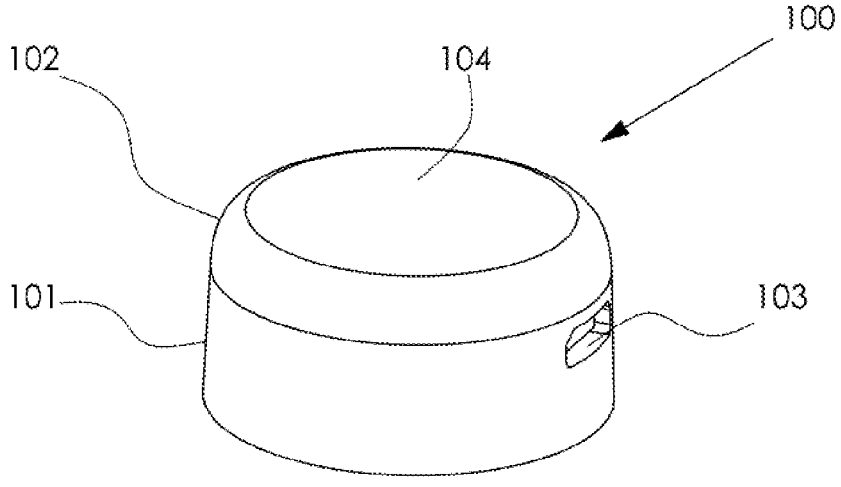
FIG. 4 is a perspective view of a sensor housing of the invention shown from a side.
Figure 5:
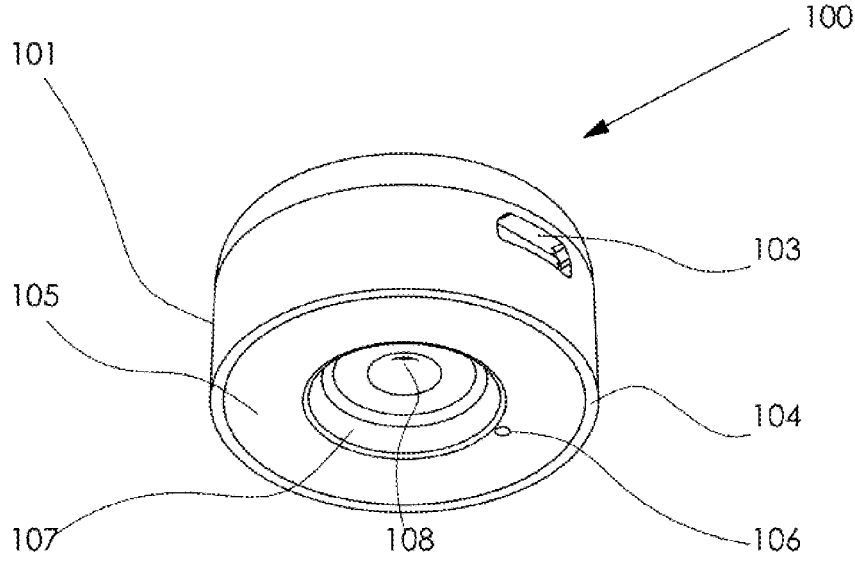
FIG. 5 is a perspective view of a sensor housing of the invention shown from the bottom.
Figure 6:
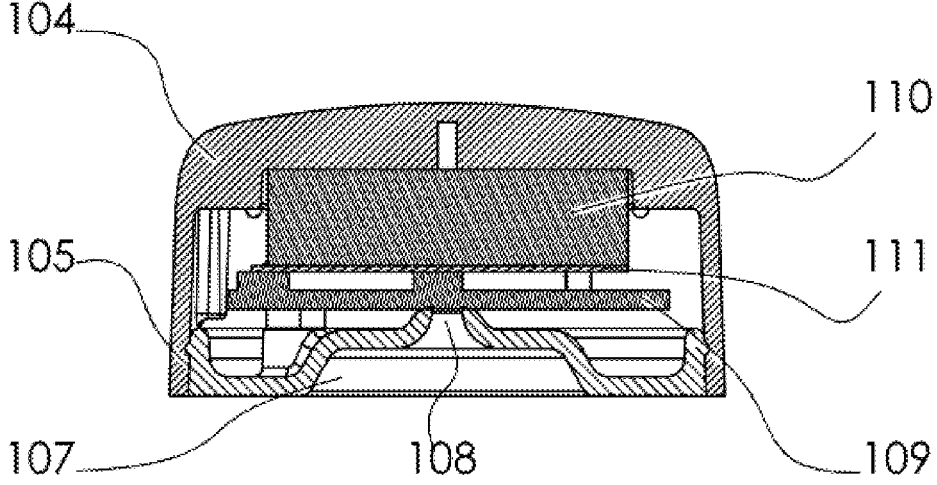
FIG. 6 is a section view through the centre of a sensor housing of the invention.

A first embodiment of the invention is shown in general terms in FIG. 4. An enclosure 100 comprises a body portion 104 and a base portion (not shown in FIG. 4). The body portion is defined by a non-vertical annular side wall 101 joined to a planar top surface by a curved top edge 102. A charging/data transfer interface 103 is provided through the annular side wall 101. As shown in FIG. 5, the base portion 105 fits within the body portion 104 to provide a planar bottom surface. A recess or depression 107 is provided within the base portion to enable an acoustic port 108 to be spaced apart from a surface to be contacted. The base of the enclosure also has one or more entry ports 106 for access to internal components (e.g. reset switches) without having to disassemble the enclosure 100.

The body portion 104 and base portion 105 are attached together with an annular snap-fit mechanism 114/117 that allows for easy assembly during manufacture but limits accessibility to the internal components when in use or when dropped or struck. The annular snap-fit geometry 114/117 and lack of graspable features on the base portion 105 are created in such a way that engagement is possible with a limited amount of force, however, disengagement requires the destruction of all or part of the enclosure 100.

The enclosure 100 is designed to house the electronic components 109 of a very small acoustic monitoring device. A typical device, as shown in cross section in FIG. 6, will be formed of one or more acoustic transducers, such as MEMS microphones, associated electronic circuitry 109 and a power source 110. In embodiments provided with multiple acoustic transducers, some of the acoustic transducers will aim to "capture" the acoustic signal of interest, whereas others will aim to "capture" acoustic interference. The efficiency of these processes will be affected by the specific location of each transducer (this will determine the relative position to the acoustic source of interest); the relative position of each acoustic transducer with respect to one another (for example the further they are apart the more likely the signal of interest for that transducer is to be corrupted by signals from other transducers); and the internal acoustic surroundings (different air gaps are going to lead to differences in transmission of acoustic signals). In embodiments of the invention, a hole facing the transducer sensing port (although several holes could be applied to a plurality of them) is present at the bottom of the base portion 105 of the enclosure. The hole will be of such dimension, that any internal active track that could violate a safety constraint as per 60601-1 would not be an accessible part. In addition to this, the attachment area is distributed between an all-around attachment area, and a hollow well, or recess, with typical height could be 2.5 mm. Note that the shape of this hollow region does not need to be circular. Surrounding the recess is a flat area configured to enable optimum attachment to a user's body.

The different acoustic transducers will be followed by conditioning circuitry 109 (mostly amplifiers and filters, although there could also be algorithms implemented in analogue processing the signal), prior to analogue-to-digital conversion, to prepare the signal (raw or processed) for wireless transmission. A microcontroller (or equivalent chip) will provide the control signals for different circuit blocks as well as the transmitter chip. In addition to all of this, some peripheral circuitry might be required, such as voltage regulators to provide biasing signals, LEDs to provide battery status, and charging and protection circuitry, passive components for noise and interference reduction as well as to optimise transmission, an antenna, and a power source 110 (such as a rechargeable battery).

Figure 7:
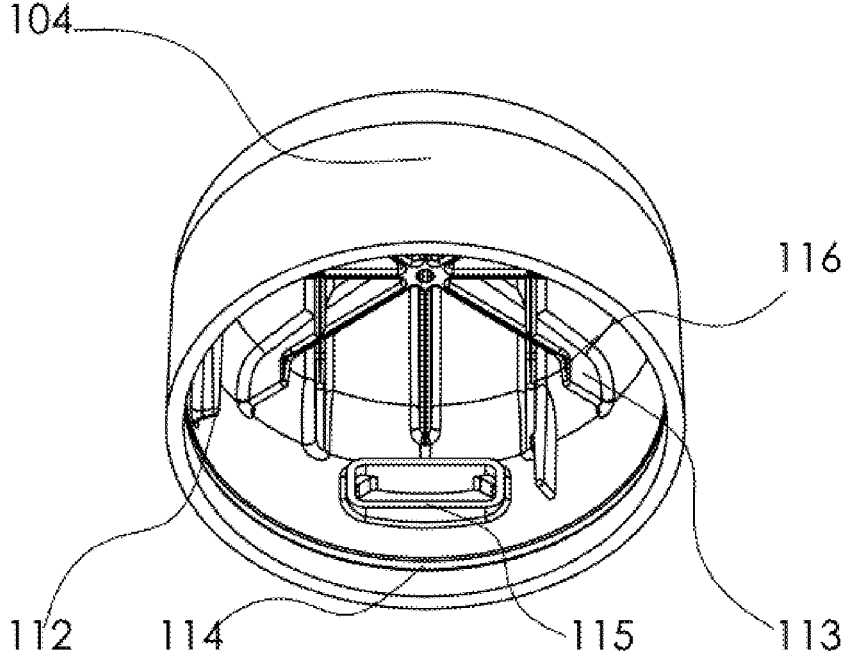
FIG. 7 is a perspective view of a body enclosure of a sensor housing of the invention shown from the bottom.

The body portion 104, as shown in FIG. 7, has multiple ribs 113 extending horizontally across the inside thereof. These ribs increase the strength and rigidity of the enclosure and provide mechanical constraints for one or more of the internal components. During assembly, electronic components such as batteries 110 are constrained within the body enclosure with profiled sections 116 included in the internal ribs. The body enclosure also includes several vertical struts 112 attached to the inside walls which serve multiple purposes. Firstly, these struts 112 are to support and constrain the internal circuitry 109 (printed circuit boards). Some of the struts 112 constrain the circuitry 109 to correct horizontal plane within the enclosure 100 and some of the struts 112 constrain the rotation of the circuitry 109 within the enclosure 100. This constraining of the circuitry 109 ensures that all components are aligned correctly to perform their respective function, for example the alignment of the programming or charging ports with the opening 103 in the enclosure 100. Secondly, these struts 112 are to strengthen and stiffen the enclosure 100. Importantly, the vertical geometry of these struts 112 minimises their mass and volume so that the overall mass of the enclosure 100 is reduced while also avoiding obstruction of the wireless communication any more than is necessary.

Figure 8:
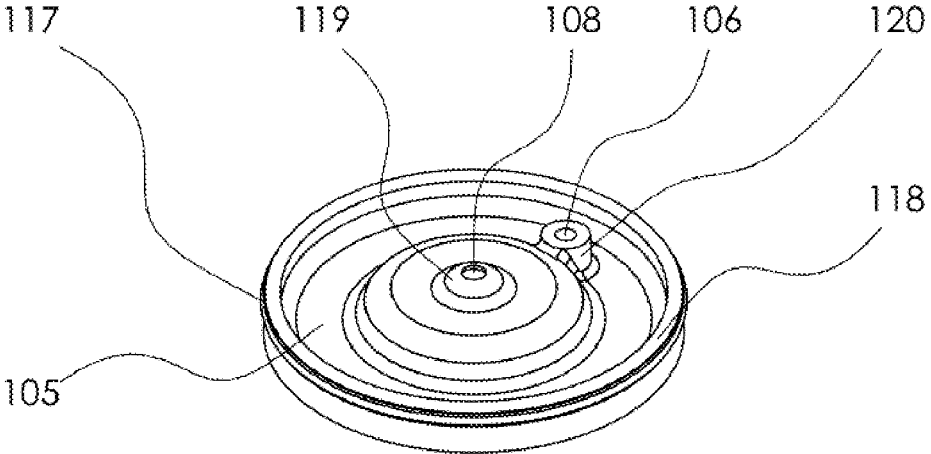
FIG. 8 is a perspective view of a base enclosure of a sensor housing of the invention shown from the top.
Figure 9:
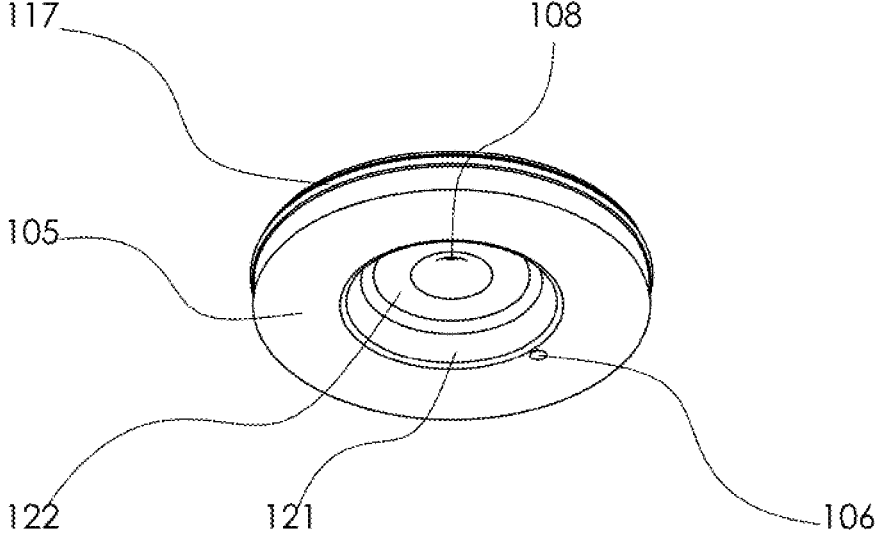
FIG. 9 is a perspective view of a base enclosure of a sensor housing of the invention shown from the bottom.
Figure 23:
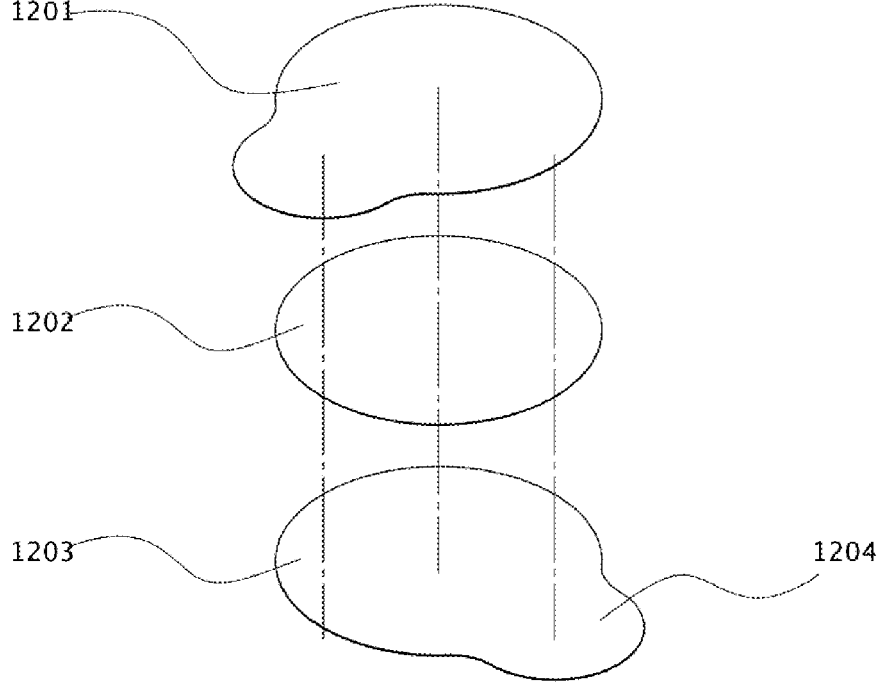
FIG. 23 is an exploded view of an adhesive pad of an embodiment of the invention.
Figure 24:
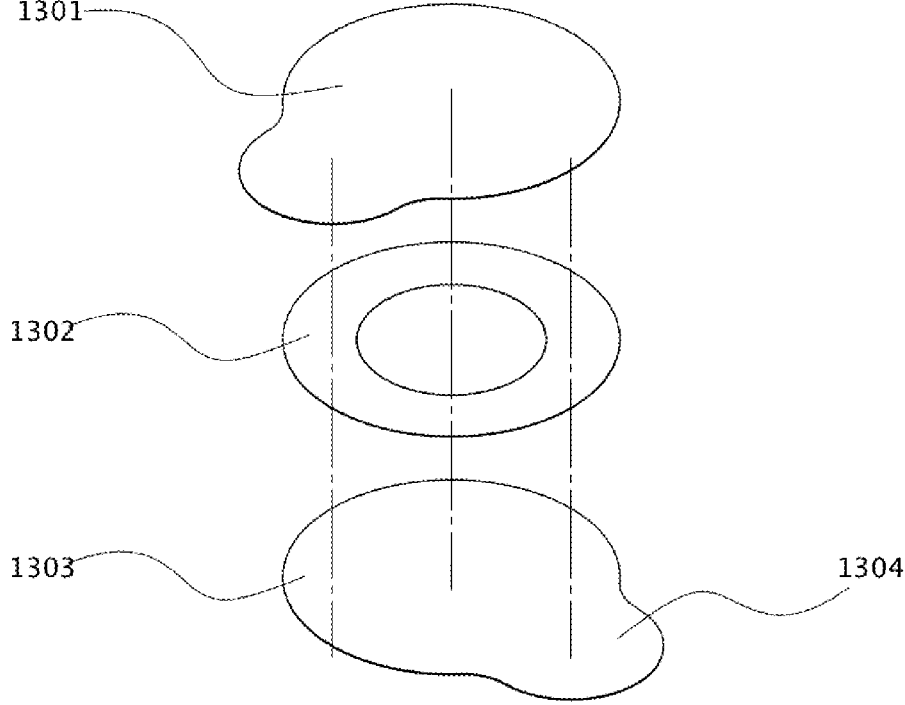
FIG. 24 is an exploded view of an adhesive pad with internal hold of for securing a sensor housing of the invention to a subject.

The base portion, as shown in FIGS. 8 and 9, includes a wide flat interface area for the attachment of adhesive pads (as shown in FIGS. 23 and 24). The recess in the base portion, can have angled or vertical side walls 121 and a flat or curved top surface 122 that leads into a central hole 108 that interfaces with the electronic componentry 109. The recess is part of the chamber, (when in contact with a surface) and its dimensions are much larger than the dimensions of the acoustic port of the acoustic transducer.

The interface between the recess and the internal electronic circuitry 109 may be formed with a lip 119 that presses against the electronic circuitry, or other internal components. The geometry and location of this lip 119 is designed in such a way that it ensures a good acoustic transmission from the base portion to the sensing circuitry 109. The geometry and location of this lip 119 also function as pre-load/elastic clamping mechanism to constrain the position and orientations of the internal components. An elastic or compressible sheet material 111 can be included between different components of the electronic assembly to assist in damping the internal components and accommodate for any small manufacturing variations in the component's geometries. This material can also function as a mechanical, electrical or thermal insulator.

Figure 10:
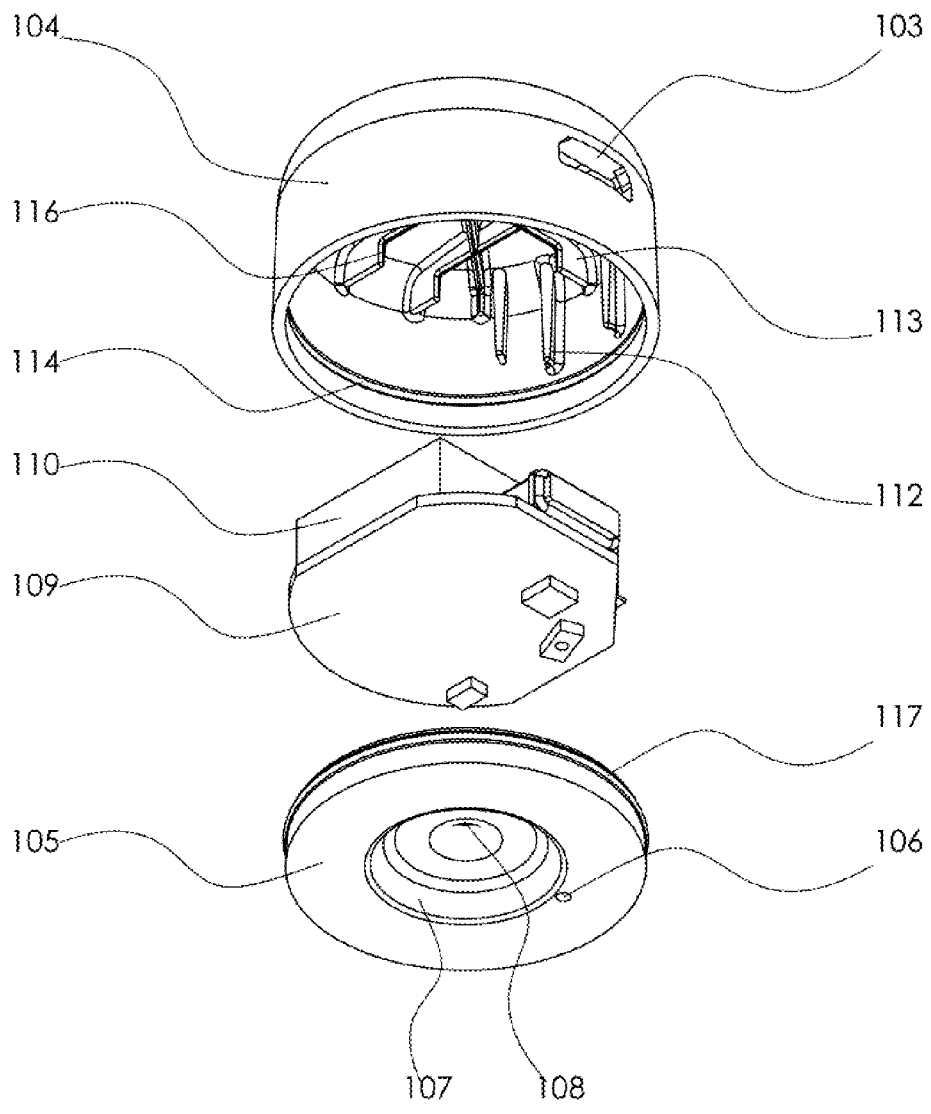
FIG. 10 is an exploded view of a sensor housing of the invention.

As shown in FIG. 10, the internal components including the internal circuitry 109 and power source 110, are pre-configured into a single unit for ease of insertion into the body portion 104 of the enclosure. Once the internal components are constrained in the correct location by the vertical struts 112 and horizontal ribs 113, the base portion 105 is snap fitted to the body portion 104.

Figure 11:
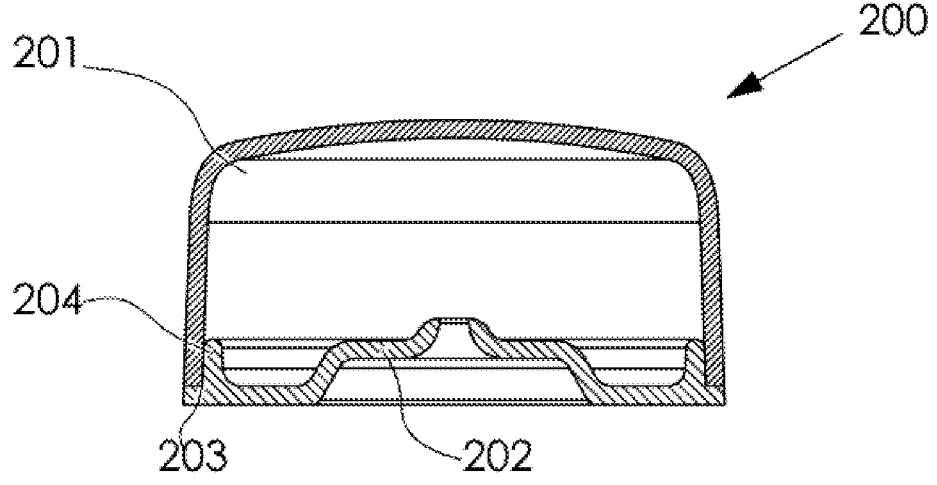
FIG. 11 is a section view through the centre of an enclosure from a sensor housing of the invention with a modified assembly method.

Another embodiment of the invention is shown in cross-section in FIG. 11. An enclosure 200 comprises a body portion 201 and a base portion 202 secured together through surface bonding techniques such as ultrasonic welding or adhesive. The base portion 202 includes an annular projection 204 extending perpendicularly from the contact surface of the base portion 202. The annular projection 204 is configured to either sit inside the body portion 201 or around outside of the body portion 201 (FIG. 11 shows the annular projection 204 sitting inside the body portion 201). This configuration allows for the accurate alignment of the body and base portions of the enclosure to ensure correct signal transmission and functionality, and provides an increased surface area 203 for the surface bonding method to engage with, thus providing strength and resisting separation of the body portion 201 and base portion 202.

Figure 12:
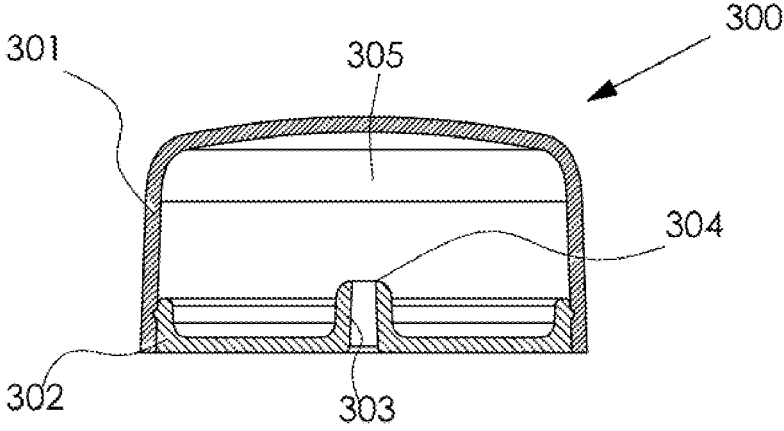
FIG. 12 is a section view through the centre of an enclosure from a sensor housing of the invention with a modified well in the bottom.

Another embodiment of the invention is shown in cross-section in FIG. 12. An enclosure 300 comprises a body portion 301 and a base portion 302 secured together either through a snap-fit interface or surface bonding techniques. The base portion 302 includes a substantially planar surface and an elongate inward depression having a channel 303 therethrough. The channel 303 has either substantially straight or angled sidewalls configured to direct air pressure from an acoustic event directly into the acoustic sensing circuitry 304. This embodiment maximises the acoustic transmission efficiency from the user to the internal sensing electronics 304.

Figure 13:
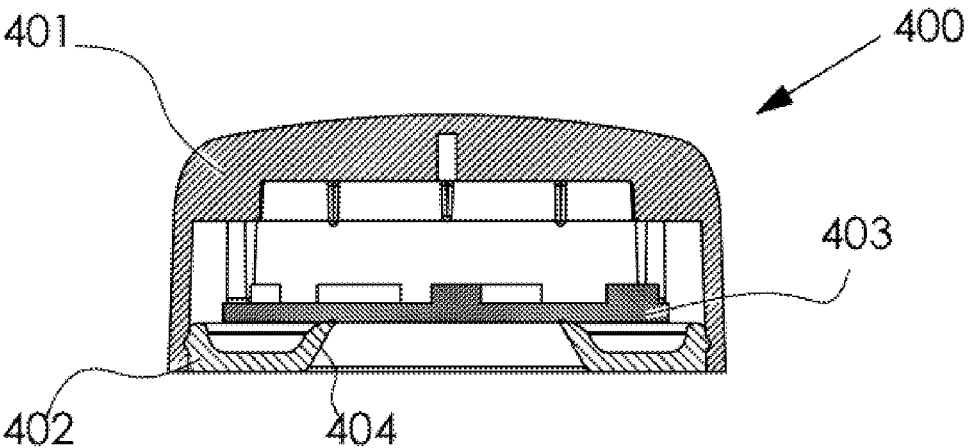
FIG. 13 is a section view through the centre of an enclosure from a sensor housing of the invention with a further modified well in the bottom.

Another embodiment of the invention is shown in cross-section in FIG. 13. An enclosure 400 comprises a body portion 401 and a base portion 402 secured together either through a snap-fit interface or surface bonding techniques. The base portion 402 includes a recess with angled sidewalls 404 that defines a large opening configured to interface directly with the acoustic sensing circuitry 403. This embodiment provides a space efficient stepped profile for the depression by combining with the bottom surface of the internal electronic circuit board 403. The side walls 404 of the depression are part of the base portion 402, and press against the electronic circuit board 403 at a larger diameter than in embodiment 100. The depression formed by the combination of the base portion 402 and the internal electronic circuit board 403 can have the same air volume characteristics as in embodiment 100, with a reduced vertical dimension, i.e. less than 2.5 mm.

Figure 14:
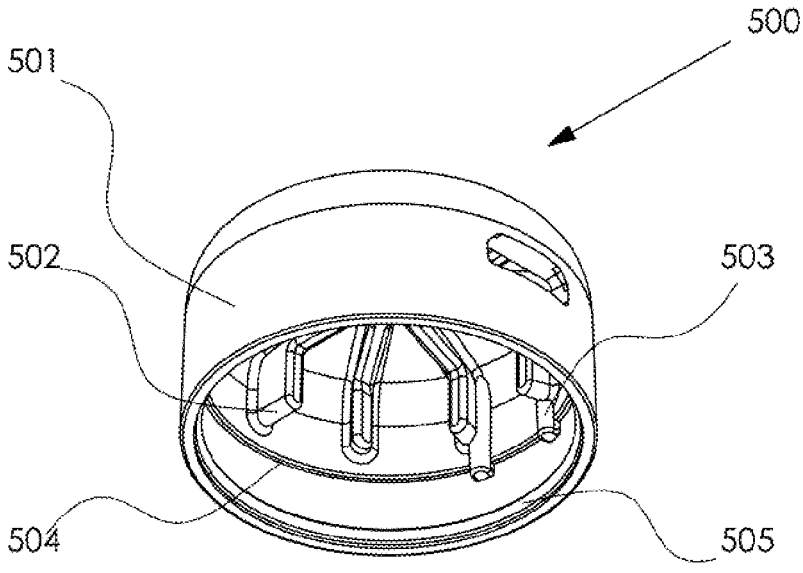
FIG. 14 is a perspective view of a body enclosure of a sensor housing of the invention with increased strength and rigidity, shown from the bottom.
Figure 15:
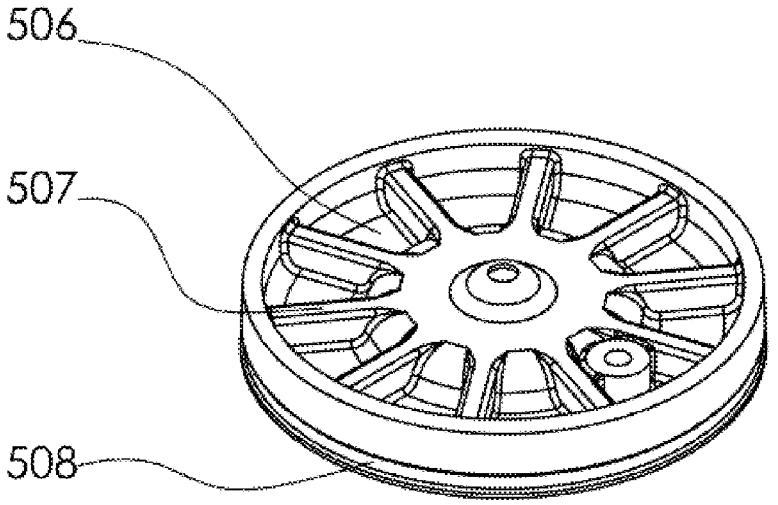
FIG. 15 is a perspective view of a base enclosure of a sensor housing of the invention with increased strength and rigidity, shown from the top.
Figure 16:
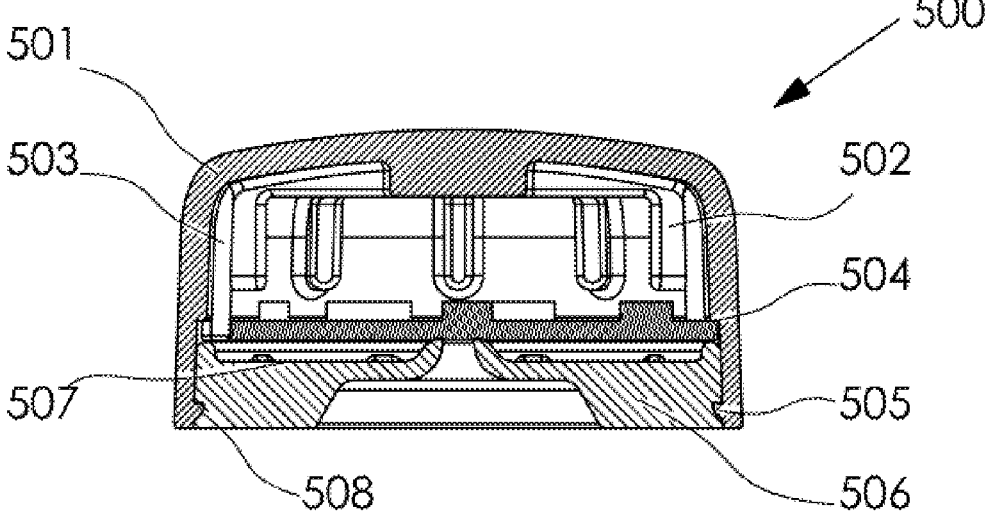
FIG. 16 is a section view of the body enclosure, base enclosure and internal electronics of a sensor housing of the invention with increased strength and rigidity.

Another embodiment of the invention is shown in FIGS. 14, 15 and 16. An enclosure 500 has several features to enhance strength and allow the enclosure 500 to withstand greater impact and crushing. This embodiment has an increased number and depth of ribs 502 inside the body portion 501, compared to embodiment 100, and has the addition of radial ribs 507 in the base portion 506. Additionally, this embodiment has a stepped lip 504 on the inside of the body portion 501 to constrain the internal electronic circuitry. This stepped lip 504 provides for a significantly increased contact area with the circuitry and therefore greater constraining. The base portion 506 in this embodiment has an increased sized outer insert that presses against the base of the internal electronic circuitry. Combining the increased sized outer insert of the base portion 506 with the stepped lip 504 on the inside of the body portion 501 creates a mechanical reinforcement that distributes impact and crush loads all the way through the enclosure 500. This embodiment also includes increased sized support struts 502, as compared to embodiment 100, in the body portion 501 to provide a greater resistance to crushing loads. Embodiment 500 includes a greater strength annular snap-fit design to ensure that the components do not separate during loading. This snap-fit is provided by an annular groove 508 in the base portion and an annular protrusion 505 in sidewall of the body portion 501 to avoid any thin wall sections in the externally exposed body portion 501. Additionally, the snap-fit protrusion 505 has an asymmetric hooked profile that requires significantly more force to disassemble than assemble.

Figure 17:
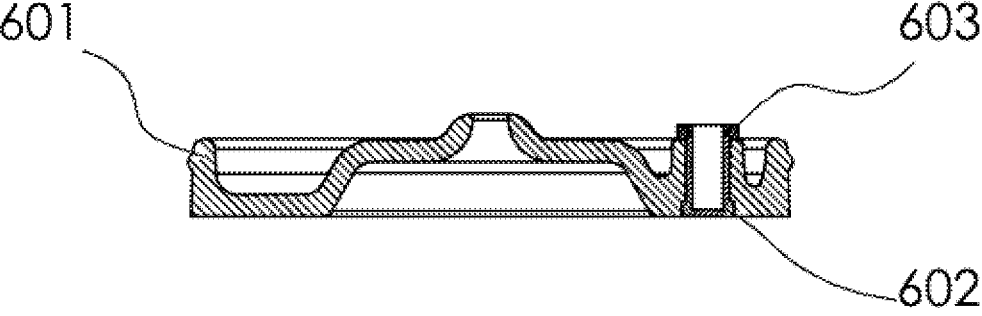
FIG. 17 is a section view through the centre of a base enclosure of a sensor housing of the invention with an optical port.

Another embodiment of the invention is shown in FIG. 17. An enclosure 600 includes a base portion 601 that has a covered port 602 to allow light transmission from internal components to the bottom surface of the base portion 601 while maintaining a level of ingress protection. The covered port 602 is created by the combination of a transmissive optical device (e.g. lens) 603, a corresponding hole through the enclosure base and a method of retaining the optical device within the enclosure 600. The method of retaining the optical device could include adhesive, retaining clips, retaining tabs, and a snap-fit mechanism or by alignment of the optical device with other internal components such that it is constrained within the enclosure. This design can be configured so that the bottom surface of the transmissive optic 603 is flush with the bottom surface of the enclosure base to ensure correct adhesion and minimise any corruption to certain optical signals. The acoustic monitor may have indicator lights that indicate various items, such as power, communication or other status items. The enclosure 600 might be designed with a material and thickness that without modification allows for the light to pass through, or the material might be thinned out in regions in which there is no violation of insulator strength for safety reasons, to facilitate the light transmission from the source, or a different translucent/transparent material might be used, as a separate part that could be assembled during fabrication. This "light optimisation area" (optical window) will generally be located either on the bottom area, or on the sides of the enclosure. Their specific location will depend on the existing internal air gaps, providing a light path from the light source to the enclosure 600, as well as on the distance from different current tracks to the specific location in the enclosure 600.

Figure 18:
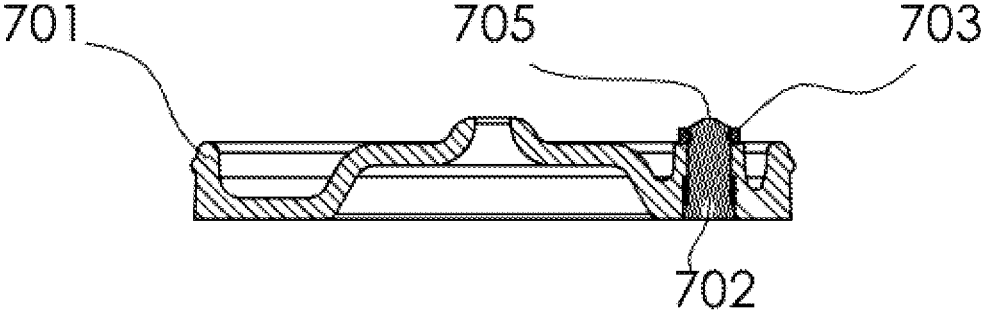
FIG. 18 is a section view through the centre of a base enclosure of a sensor housing of the invention with an integrated switch mechanism.

Another embodiment of the invention is shown in FIG. 18. An enclosure 700 includes a base portion 701 that has an incorporated button or switch 702 for user interfacing with internal electronic componentry while maintaining a level of ingress protection. The button or switch 702 is located into a hole in the base portion 701. The button 702 can be retained with a clip or similar mechanism 703 and can be fitted with a spring, other tensioning mechanism or sealing mechanism around its diameter. The button body is free to move vertically with a prescribed range and can be sprung loaded to return to the bottom position. The interfacing point 705 can be shaped in any required way so that, when a user pushes the body upwards, it will interface with and engage the internal electronic circuitry, as required. This action could also be formed with a contactless switch by fitting inductive or similar components to the internal surface of the base portion 701.

Figure 19:
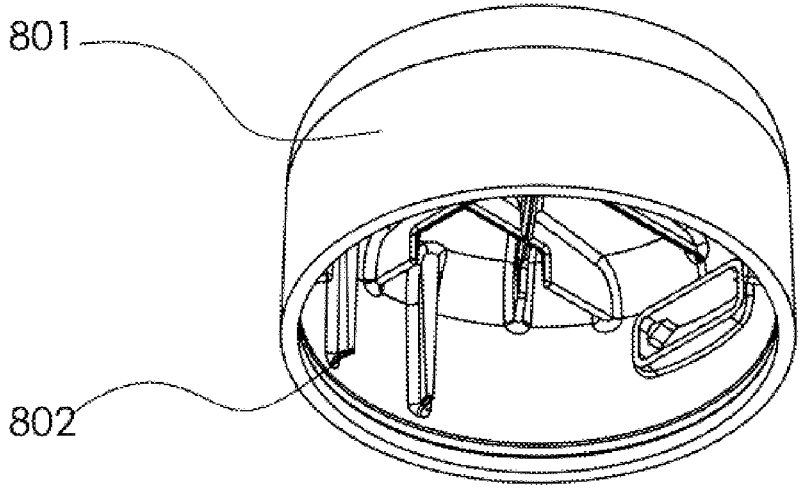
FIG. 19 is a perspective view of a body enclosure of an embodiment of the invention with rotation fixing mechanism shown from the bottom.
Figure 20:
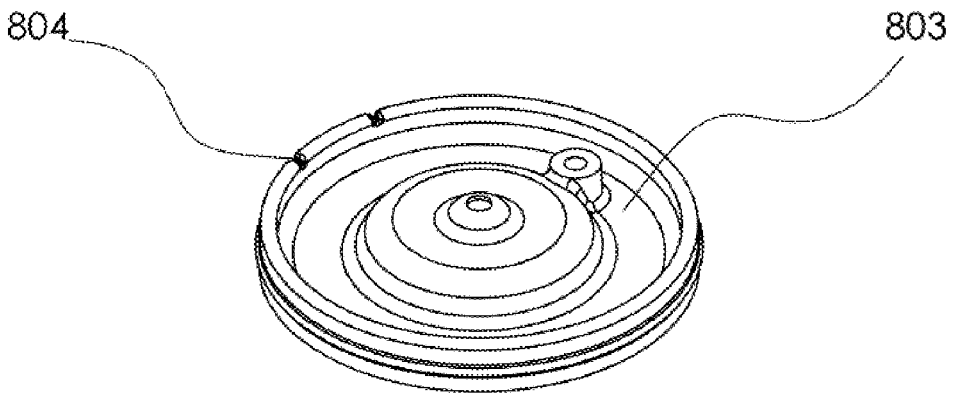
FIG. 20 is a perspective view of a base enclosure of a sensor housing of the invention with rotation fixing mechanism shown from the top.

Another embodiment of the invention is shown in FIGS. 19 and 20. An enclosure 800 comprises a keying mechanism that aids in assembly and manufacture, and ensures that all ports on the enclosure base are accurately aligned with respective receptacles, components or sensors in the internal electronic system, whilst also allowing for enclosure mass production by moulding and maintaining water ingress protection. The keying mechanism of the body portion 801 is created with one or more extended struts 802 that run from the top of the body portion 801 to a small distance from the bottom of the body portion 801. The base portion 803 has a corresponding number of U-shaped cut-outs 804 on the top of it, at the edge and at a precisely defined angle. During assembly, the U-shaped cut-outs 804 on the base portion 803 engage with the extended struts 802 on the body portion 801, constraining the rotation of the base portion 803 relative to the body portion 801, thus aligning all ports as required.

Figure 21:
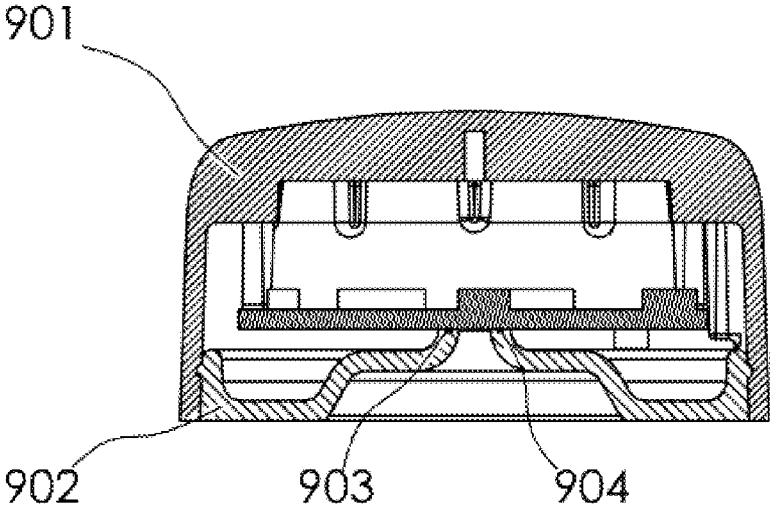
FIG. 21 is a section view through the centre of the body enclosure, base enclosure and internal electronics of a sensor housing of the invention with a sealing gasket between the well and electronic components.

Another embodiment of the invention is shown in FIG. 21. An enclosure 900 includes a body portion 901 and a base portion 902. The base portion 902 incorporates a recess in a raised lip 903 that interfaces with the electronic circuit board to allow the inclusion, constraining and effective operation of a sealing gasket or O-ring 904 between them. This arrangement minimises the possibility of pressure or air loss from the internal volume of the enclosure, thus maximising the transmission of acoustic signals from the user to the electronic sensing components.

Distributing all these components spatially for optimum performance is not a trivial task because of the complex set of different electrical, physical, usability and physiological trade-offs that have to be taken simultaneously into account. For example, the type of application for which a monitor of this kind would be most beneficial would be one requiring long term continuous monitoring. The uninterrupted duration of monitoring is, however, limited because of the duration of the power source. If choosing a battery, the duration of the power source depends both of the chemistry of the battery, the nature of the cell (primary or secondary) and its volume. The nature of the cell will have important usability implications, since secondary cells have less capacity (energy per unit of volume) but they, however, allow for the system to be recharged. The volume will affect the size of the system, as well as its weight. The result of all of this is that the battery will be the dominating component in the volume of the system. However, in most case scenarios, the shape of the batteries is fixed (customisation might be possible but this results on a significant manufacturing cost), and hence this is going to severely limit the spatial distribution of other components. But there are components that also have their own spatial requirements. The antenna is an example of those. Depending on the antenna choice a trade-off has to be found taking into account the surface area occupied by it, the gain, and the space around it that needs to be left component-free. But in addition to that, because of the size of the system, the distribution of components is always going to have an effect in the transmission that needs to be accounted for. In addition to all of this, the positioning of the transducers is going to heavily influence their effective signal to noise ratio (i.e. this would be understood as the ratio between the larger signal they can detect and the noise floor, considering that this noise floor would also account in certain instances for interference introduced by other acoustic signals). The design of the enclosure plays a very important role on getting these trade-offs right. The enclosure can significantly affect the transmission of the different acoustic signals (both, body signals of interest as well as artefact that need to be sensed so that they can be later eliminated); can "fix" the spatial location of certain components (such as batteries) in an optimum way without having to rely on special internal connectors which would compromise other component's spatial distribution; can eliminate the need of certain battery/communications or other indicators; can facilitate resetting (or changing the status) of the system; can eliminate the need of certain means of user protection which would impact on some important system trade-offs; can protect the system; can facilitate safe battery charging; and can eliminate the need of cumbersome means of user attachment.

Each part of the enclosure may be fabricated from medical grade acrylonitrile butadiene styrene (ABS) with a thickness of 1 mm. But those skilled in the art may use other types of materials without deviating from the present invention. A polished finished for the enclosure would be desirable, both for aesthetic as well as performance factor. A rugged surface finish will generate stronger acoustic artefacts, leading to more signal corruption. However, a polished finish also leads to higher production costs.

Although, with appropriate means of body attachment the acoustic transmission of body sounds will be optimised, out of the body sounds can also be picked up by the transducer. Because of this, an array (one or several) microphones might be arranged in the printed circuit board to sense those environmental noises, in order to facilitate processing and elimination. The sensing port of those transducers will generally be facing the other side of the PCB, so that they will not pick up body signals, whilst picking up noise. The enclosure might be designed to guarantee an air gap between those ports and the surface, to facilitate signal transmission.

The enclosure may have internal reinforcements in order to minimise the probability of breaking into more than one piece in the situation of a strong impact, which would allow access to electrical parts compromising safety. This internal reinforcement can simultaneously be used to guide the assembly and fix some components position to minimise hazards cause by vibrations, whilst also guaranteeing the air gaps mentioned above. An example of such is shown in embodiment 500.

Figure 22:
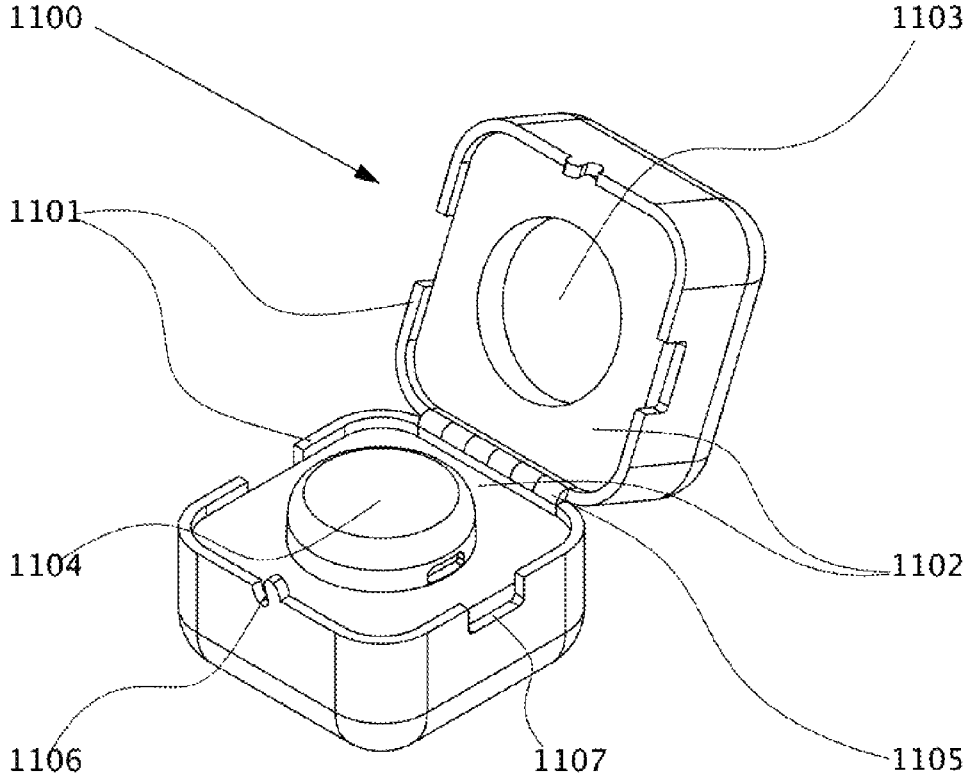
FIG. 22 is a perspective view of a sensor housing of the invention with secondary mechanical insulation.

The enclosure may be custom coloured and could include any number or combination of logos, labels or graphical designs. The logos, labels or designs could be included into the enclosure by the adhesion or attachment of any other material, such as paint or vinyl, or by the contouring of the enclosure's surface itself, such as embossing or engraving. Another embodiment of the invention is shown in FIG. 22. A secondary enclosure 1100 enables an enclosure as described in relation to FIGS. 4 to 21 (referred to in this paragraph as a primary enclosure) to be stored and transported in such a way that it has a significantly increased resistance to mechanical loading, impact and vibration. The secondary enclosure is formed from an impact resistant outer shell 1101, manufactured from a material such as ABS, and a mechanical insulating layer 1102, manufactured from a material such as low-density foam. A recess 1103 is included in both halves of the mechanical insulating layer to allow the primary enclosure 1104 to sit securely. The outer shell can be formed from a hinged design 1105 with a securing mechanism 1106 to keep the two parts of the secondary enclosure together and secure the primary enclosure in place.

Additionally, secondary holes 1107 can be placed in the side of the secondary enclosure to allow the application of cables or other connectors to the ports on the primary enclosure. This could be used for, for example, charging device batteries while the primary enclosure is inside the protective secondary enclosure.

The enclosure must also have adequate characteristics so that it can be properly attached to a subject's body without modifying the acoustic characteristics, and minimising the risk of deattachment. Attachment can be achieved by attaching an adhesive tape to the bottom of the base portion of the enclosure (when the liner is removed, the adhesive part can be put in contact with a subject's body). By doing it this way, the adhesive can serve a multiple role: keeping the enclosure in place and waterproofing/dust-proofing the microphone hole. In order to allow multiple uses (and users) the adhesive part of the enclosure must be exchangeable. There are a number of ways of achieving this, but one that is found to be very effective is to have a double taped adhesive with two tabs, as shown in FIG. 23. The absence of tabs makes it very hard for users to centre the enclosure, due to the very small size of it, and remove the liners. However, this is an important requirement, due to the very small contact area left as a consequence of the well created in the centre of the enclosure, to avoid the attenuation of the signal caused mostly by loose skin or tissue in people with larger necks.

The user would change the adhesive by using a two-sided adhesive pad with liners designed for usability of attachment to the enclosure and attachment to the user. Embodiment 1200 of the adhesive and liners is shown in FIG. 23. The liners 1201/1203 are designed with easy manipulation tabs 1204 that protrude out past the adhesive tape 1202 that are placed at an angle to each other (e.g. 90 degrees) and each are made from materials that have a different release strength to the other to allow for control over which liner will be removed first, so that clearer instructions can be given to the user. The angle of the tabs on the liner is important for ensuring easy peeling by the user. Once the first liner has been removed, the device can be placed accurately on top of the adhesive tape. After this, the user can remove the second liner by pulling on the remaining tab and attaching the enclosure to themselves. After use, the adhesive tape can be either slightly larger in size than the enclosure or have an extra tab to allow easy manipulation of the adhesive tape by the user and removal from the enclosure.

Another embodiment of the adhesive 1300 as shown in FIG. 24 has a central hole 1305 on the adhesive tape to improve the acoustic transmission into the hollow well in the base enclosure.

Figure 25:
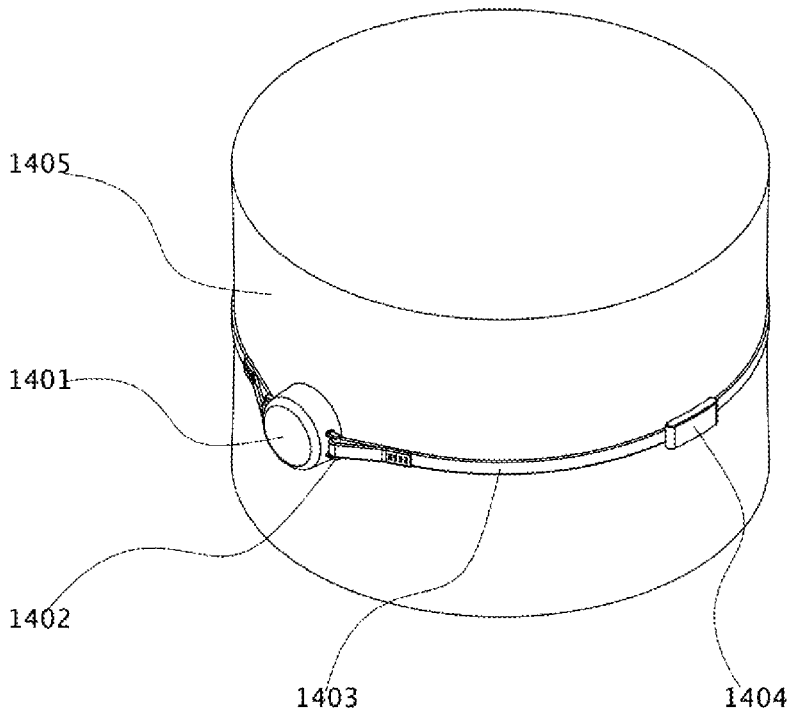
FIG. 25 is a perspective view of a sensor housing of the invention with additional fixing point and a strap.

Because this is intended for very small monitoring systems, in the specific case of pediatric application, the system itself can constitute a suffocation hazard if attached only with the adhesive/surface glue or alternative method, in which a child could take it off and put it in their mouth. In this case, a strapping mechanism, as shown in FIG. 25, may be added to the enclosure reduce the hazard. The enclosure 1400 has additional mounting points 1402 on either side of the body portion 1401 for the permanent attachment of a restraining strap 1403. This strap allows for additional security of the attachment of the enclosure to the body of a user and minimises the risk of a child removing the enclosure and inserting the enclosure into its mouth. The strap can be made of any material that will comfortably enclose the body of the user 1405 and can be attached with the use of a clip, hook-and-loop fasteners or any other form of strap fastener 1404.

The enclosure of FIGS. 4 to 21 is suited for attachment to the palm facing side of subject's wrist such that a sensor or sensor enclosed therein are located in close proximity with the subject's arteries. An example of means for attaching the enclosure to the subject's forearm is shown in FIG. 25 includes a strap configured for attachment around the subject's forearm, the strap having an opening for receiving the enclosure and allowing limited positional and rotational motion of the enclosure relative to the strap when the strap is in a first configuration. The enclosure can either be pre-attached to the strap when the strap is positioned around the subject's wrist or the enclosure can be inserted into the strap after the strap has been positioned around the subject's wrist in its first configuration. Such limited motion of the enclosure relative to the strap enables the subject to move the enclosure into a position where a good acoustic signal is received from the subject's arteries by the acoustic sensor within the enclosure.

Signals transmitted from the apparatus or stored and displayed on the apparatus are processed through signal processing algorithms to provide subject's readable data that can be interpreted into physiological information either by the user of the apparatus or a healthcare professional. The signal processing techniques can be run on the apparatus to reduce the need for transmission of data to external devices or run on a remote computer or device to minimise the necessary processing power of the apparatus. The algorithms use signal processing methods for extracting useful physiological parameters from the acoustic signals. Several methods are used for different parts of the algorithm. For example, acoustic signal from continuous monitoring needs to be pre-processed to remove noise and motion artefacts. This may use information from other sensors, for example microphone and motion sensors, to infer contextual information followed by application of filters specific to different activities. The algorithms use both narrow and wide band filtering to segment sections of acoustic signal that are representative of cardiac and respiratory events. The segmentation process is followed by feature extraction within each area of interest. It included extraction of features in time and frequency domains such as amplitude, zero crossing, signal gradient, spectral power, energy, entropy, spectral edge frequency, wavelet coefficients, MFCC coefficients, amongst others. The features are then classified using a classifier that may be different for each event. For example, the respiratory event may be classified using a logistic regression model while a cardiac event may be classified using support vector machine. For blood pressure monitoring, the algorithms also look for rate of change in certain features in the acoustic signal from a resting position. Using more information about the applied air pressure, this is then subsequently used to derive systolic and diastolic blood pressure values.

Another aspect of the invention comprises a blood pressure cuff incorporating the apparatus described above. Such a blood pressure cuff may comprise an inflatable rubber bladder that is fastened around a subject's arm or the strap itself may comprise an inflatable cuff. Either a manual or powered pump is used to inflate the rubber bladder. After inflation, an air valve allows air pressure from within the inflated rubber bladder to be slowly released. Apparatus according to aspects of the invention is used to measure blood flows in one or more target blood vessels. As the heart beats it pushes blood through blood vessels thus resulting in a rise and fall of blood pressure. The apparatus of the invention can replace a traditional stethoscope in listening to blood flow sounds, such as turbulence when measuring blood pressure. Traditionally, when the rubber bladder is inflated it exerts a pressure on the target blood vessels above the maximum arterial pressure, i.e. systolic pressure. At maximum inflation, blood flow through the target blood vessels is completely cut off hence the apparatus will not detect any acoustic signals. As the pressure of the rubber bladder is relieved such that the pressure exerted by the rubber bladder equals the arterial systolic pressure, blood is able to flow past the cuff. At this point, the apparatus will begin to identify acoustic signals associated with blood turbulence caused by the blood flowing past the cuff. The acoustic signals will continue until the air pressure of the rubber bladder falls below the lowest blood pressure, i.e. diastolic pressure. At this point no further acoustic signals are detected.

To measure blood pressure, the air pressure of the inflatable bladder at the point blood is able to flow past the cuff, i.e. when acoustic signals caused by blood turbulence are heard, is recorded. This process is typically undertaken manually. Using the present invention, the patient's systolic and diastolic blood pressures can be automatically extracted upon the apparatus measuring an acoustic signal in respect of systolic pressure and ceasing to measure an acoustic signal in respect of diastolic pressure.

The apparatus (10) may also be used in conjunction with one or more other cardiac sensors to measure pulse transient time from one location within the subject's body to another location. For example, a cardiac sensor may be located on a subject's chest. The cardiac sensor measures the subject's pulse at that location. The apparatus (10) then measures the subject's pulse in a target blood vessel on the forearm or in the thigh area, for example. The measured pulse transient time is then extrapolated to provide an indication of blood pressure. Blood pressure can thus be monitored over time through constant or periodic monitoring and negating the need to use conventional blood pressure measurement devices such as inflatable cuffs.

The foregoing description is given by way of example only and is not intended to limit the scope of the claims.

What is claimed is:

1. Apparatus for measuring physiological parameters in a blood vessel of a subject, the apparatus comprising:
   a means for attachment of the apparatus on a part of the subject's body;
   at least one acoustic sensor positionable on the part of the subject's body and configured to receive an acoustic signal from the blood vessel, the at least one acoustic sensor comprising:
   a first microphone positioned to measure an acoustic signal from the blood vessel,
   a second microphone positioned to measure ambient background noise, and a processor for receiving signals from the first microphone and the second microphone, the processor being configured to generate a noise-reduced acoustic signal by subtracting the background noise measured by the second microphone from the acoustic signal measured by the first microphone;

an optical sensor comprising a light source, and comprising a photosensor configured to measure one or more properties of the light source through absorption, refraction, or reflection of the light source from the blood vessel; and a motion sensor for determining whether the apparatus is being worn by a subject;

wherein the apparatus is configured to activate the optical sensor only when the motion sensor determines motion representative of the apparatus being worn by the subject; and wherein the apparatus is configured to activate the first microphone and the second microphone only when the optical sensor determines light absorption, refraction, or reflection representative of the apparatus being located in close proximity to the blood vessel.

2. The apparatus according to claim 1, wherein each of the first microphone and optical sensor are mounted on a common surface and facing a portion of the subject's body surface.

3. The apparatus according to claim 1, wherein the means for attachment of the apparatus on a part of the subject's body comprises means for attachment of the apparatus on a limb of the subject.

4. The apparatus according to claim 1, wherein the means for attachment of the apparatus on a part of the subject's body comprises a sensor housing and an attachment interface, the attachment interface having a first attachment configuration and a second attachment configuration such that, in the first attachment configuration, the sensor housing can be moved in three degrees of freedom relative to the attachment interface, and in the second attachment configuration, the sensor housing is positionally fixed relative to the attachment interface.

5. The apparatus according to claim 4, wherein the sensor housing further comprises sealing means configured to provide an air tight seal between the sensor housing and the subject's body surface.

6. The apparatus according to claim 4, wherein the sensor housing comprises a sidewall having at least one opening and open upper and lower surfaces to permit insertion of the acoustic sensor into the sensor housing when the attachment interface is in the first attachment configuration.

7. The apparatus according to claim 6, wherein at least one of the at least one openings in the sidewall is fitted with a lens.

8. The apparatus according to claim 1, further comprising a transmitter for sending acoustic signals measured by the acoustic sensor to an external electronic device.

9. The apparatus according claim 1, wherein the apparatus is configured to activate one or more additional electronic components when the photosensor determines one or more properties of light representative of the apparatus being located in close proximity to an artery or vein.

10. The apparatus according to claim 1, wherein the acoustic sensor is configured to measure acoustic signals in the range of 10 Hz to 10 KHz.

11. The apparatus according to claim 1, wherein the apparatus is configured to be worn on the subject's forearm.

12. A system for measuring physiological parameters in a blood vessel comprising the apparatus according to claim 1 and an electronic device configured to receive signals from the apparatus and display one or more data field representative of physiological parameters measured by the apparatus.

13. A method of measuring physiological parameters in a blood vessel using the apparatus according to claim 1, the method comprising:

using the motion sensor to determine whether the apparatus is being worn;

activating the optical sensor only in response to determining that the apparatus is being worn;

using the optical sensor to determine a position of the apparatus relative to the blood vessel;

activating the first microphone and the second microphone only when the optical sensor determines light absorption, refraction, or reflection representative of the apparatus being located in close proximity to the blood vessel;

using the first microphone to measure the acoustic signal from the blood vessel;

using the second microphone to measure ambient background noise; and subtracting the ambient background noise measured by the second microphone from the acoustic signal measured by the first microphone to generate the noise-reduced acoustic signal.

* * * * *